United States Patent [19]

Tsumanuma et al.

[11] Patent Number: 5,742,429
[45] Date of Patent: Apr. 21, 1998

[54] DEVICE FOR STEREOSCOPIC VISUALIZATION INCLUDING A STEREOMICROSCOPE AND FIBERSCOPE

[75] Inventors: Takashi Tsumanuma, Sakura; Kennichi Nakatate, Yachimata; Hiroyoshi Koyama, Tokyo, all of Japan

[73] Assignee: Fujikura Ltd., Tokyo, Japan

[21] Appl. No.: 596,239
[22] PCT Filed: Jul. 12, 1995
[86] PCT No.: PCT/JP95/01389
§ 371 Date: Mar. 7, 1996
§ 102(e) Date: Mar. 7, 1996
[87] PCT Pub. No.: WO96/02863
PCT Pub. Date: Mar. 1, 1996

[30] Foreign Application Priority Data

Jul. 13, 1994 [JP] Japan ................. 6-161580

[51] Int. Cl.$^6$ ............................. G02B 21/22
[52] U.S. Cl. ........................... 359/377; 359/381
[58] Field of Search .................. 359/372–377, 359/381

[56] References Cited

U.S. PATENT DOCUMENTS

| 2,143,632 | 1/1939 | Ott ............... 359/381 |
| 4,834,518 | 5/1989 | Barber ............ 359/375 |
| 5,095,887 | 3/1992 | Leon et al. ....... 359/375 |

FOREIGN PATENT DOCUMENTS

| 0418109 | 3/1991 | European Pat. Off. . |
| 2681150 | 3/1993 | France . |
| 1942971 | 2/1970 | Germany ........... 259/376 |
| 5-333270 | 12/1993 | Japan ............. 359/372 |

Primary Examiner—Jon W. Henry
Attorney, Agent, or Firm—Sprung Kramer Schaeffer & Briscoe

[57] ABSTRACT

The device for stereoscopic visualization according to the present invention enables an observer to see both an image from a stereomicroscope and an image from a stereoscopic fiberscope without removing his eyes from the eyepieces. The device for stereoscopic visualization may be used in surgical procedures.

3 Claims, 10 Drawing Sheets

DEVICE FOR STEREOSCOPIC VISUALIZATION INCLUDING A STEREOMICROSCOPE AND FIBERSCOPE

TECHNICAL FIELD

The present invention relates to a device for stereoscopic visualization which enables stereoscopic observation of an object. In particular, the present invention relates to a device for stereoscopic visualization wherein the observer can observe a view of the image from a stereomicroscope and a view of the image from a stereoscopic fiberscope, without having to remove his eyes from the eyepieces.

BACKGROUND ART

Surgery on the eyes, brain and other areas demands extremely delicate techniques, and thus, in recent years has been carried out while employing a stereomicroscope to observe the affected area.

As shown in FIG. 15, a stereomicroscope has at least a pair of eyepieces 1 and a pair of objectives 2, through which a left eye optical path $8l$ and a right eye optical path $8r$ pass, the left eye optical path $8l$ corresponding to the left eye and the right eye optical path $8r$ corresponding to the right eye of the observer 7.

Further, the angle defined by the observed object S1 and the optical axes of the two objectives 2 is designated as the angle of visibility$\alpha$, while the angle defined by the observed object S2 and the optical axes of the two objectives 2 is designated as the angle of visibility$\beta$. The angle of visibility$\alpha$ for observed object S1, which is at a position closer to the observer, is larger than angle of visibility$\beta$. The difference between these two angles is designated as the angle visibility difference$\theta$.

The observer 7 recognizes the angle visibility$\theta$ difference as the difference between his distance from observed object S1 and observed object S2. As a result, the observer is able to view the observed object stereoscopically.

Endoscopes (fiberscopes), which in general are widely used in medical exams and treatments, primarily of the digestive system, are increasing in importance. In particular, ultrathin endoscopes of less than 1 mm in diameter have been developed in recent years. These endoscopes can be used not only in the digestive system, but also in areas previously not possible such as extremely narrow, fine lumen, for example, blood vessels, mammary glands, pancreatic ducts, inside the eye, and vessels in the brain.

Accordingly, in delicate surgeries carried out in recent years, a stereomicroscope has been employed to observe the entire image of the surgical area, while an endoscope has been employed for detailed examination.

However, when performing surgery using an endoscope, the difficulty of a delicate operation is compounded if a sense of distance from the image cannot be imparted to the observer.

Thus, the ability to visualize an object stereoscopically is necessary when employing an endoscope as well. Thus, as in the case of the stereomicroscope described above, a stereoscopic endoscope provided with a two system fiberscope for the left and right eyes of the observer was developed.

The principle behind one example of this device will now be explained with reference to FIG. 16. The stereoscopic endoscope explained in FIG. 16 is provided with eyepieces 3, guided optical paths 4 comprising an optical fiber, objectives 5 and a light guide 6 for the purpose of illumination.

Left eye optical path $8l$ and right eye optical path $8r$, corresponding to the left and right eyes of the observer 7, pass through eyepieces 3, guided optical paths 4 and objectives 5.

The angle visibility difference$\theta$ between the angle of visibility$\alpha$ defined by the Observed object S1 and the optical axes of the two objectives 5 and the angle of visibility$\beta$ defined by the observed object S2 and the optical axes of the two objectives 5 is recognized by the observer 7 as the difference in his distance from observed object S1 and observed object S2, thus enabling stereoscopic visualization.

The combined employment of a stereomicroscope and a stereoscopic endoscope has been increasing.

However, in order to use a stereoscopic endoscope after using a stereomicroscope, the observer must shift to the stereoscopic endoscope by removing his eyes from the stereomicroscope for a time. Conversely, in order to use a stereomicroscope after using a stereoscopic endoscope, the observer must remove his eyes from the stereoscopic endoscope for a time in order to look into the stereomicroscope. For this reason, in order to use a stereomicroscope and a stereoscopic endoscope together, the eyes must be moved between the two devices, which is bothersome. Moreover, each time the eyes move from one device to the other, a certain amount of time must be required for the field of vision and focus to readjust. Thus, the surgery procedure is lengthened by the time required to shift between devices and for vision adjustment, increasing the stress on the surgeon.

DISCLOSURE OF INVENTION

The present invention was conceived in order to resolve the aforementioned problems, and has as an object the provision of a device for stereoscopic visualization which enables observation through a stereomicroscope and observation through a stereoscopic endoscope to be carried out without requiring the observer to shift his eyes. In one aspect of the present invention, the optical path of the eyepiece is joined with one of either the optical path of the stereomicroscope or the optical path of the stereoscopic fiberscope by means of the operation of an optical path switcher, so that the eyes are never removed from the eyepieces. Thus, by means of a simple operation, the observer can alternately view the image from a stereomicroscope and the image from a stereoscopic fiberscope.

Further, in another aspect of the present invention, a reflecting mirror which transmits light rays from the stereoscopic fiberscope to the eyepiece is provided along the optical path which joins the objective and the eyepiece of the stereomicroscope. As a result, the image from the stereoscopic fiberscope can be formed inside the image from the stereomicroscope. Accordingly, the observer does not need to remove his eyes from the eyepieces, but is able to simultaneously observe the image from the stereomicroscope and the image from the stereoscopic fiberscope.

3

Figure 6:
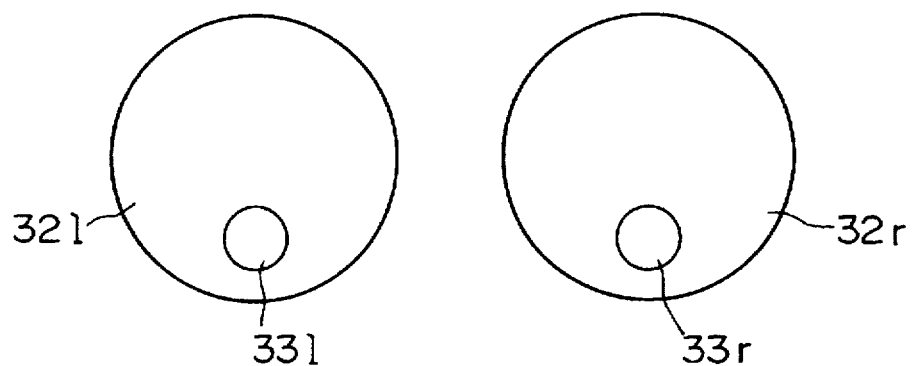

FIG. 6 is a plan view showing the image shown in the eyepieces.

Figure 7:
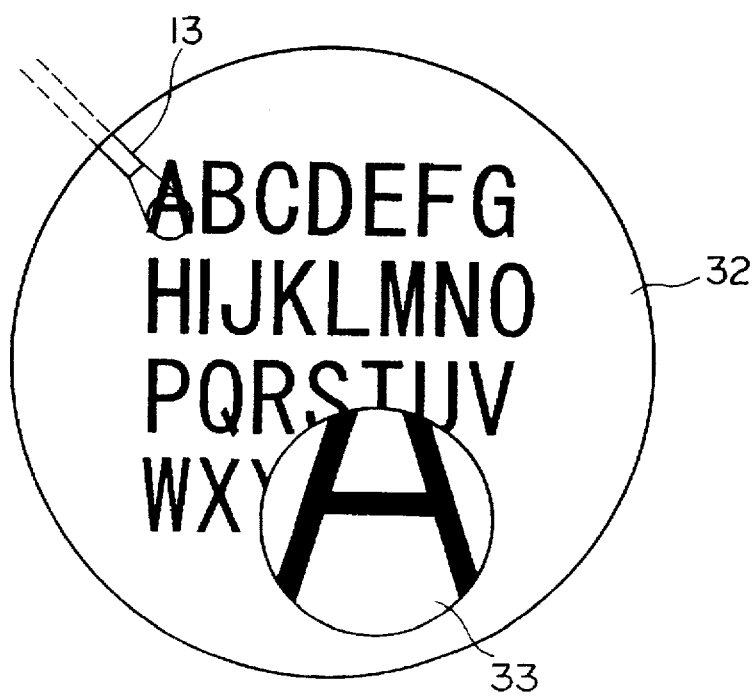

FIG. 7 is a plan view showing the image recognized by the observer.

Figure 8:
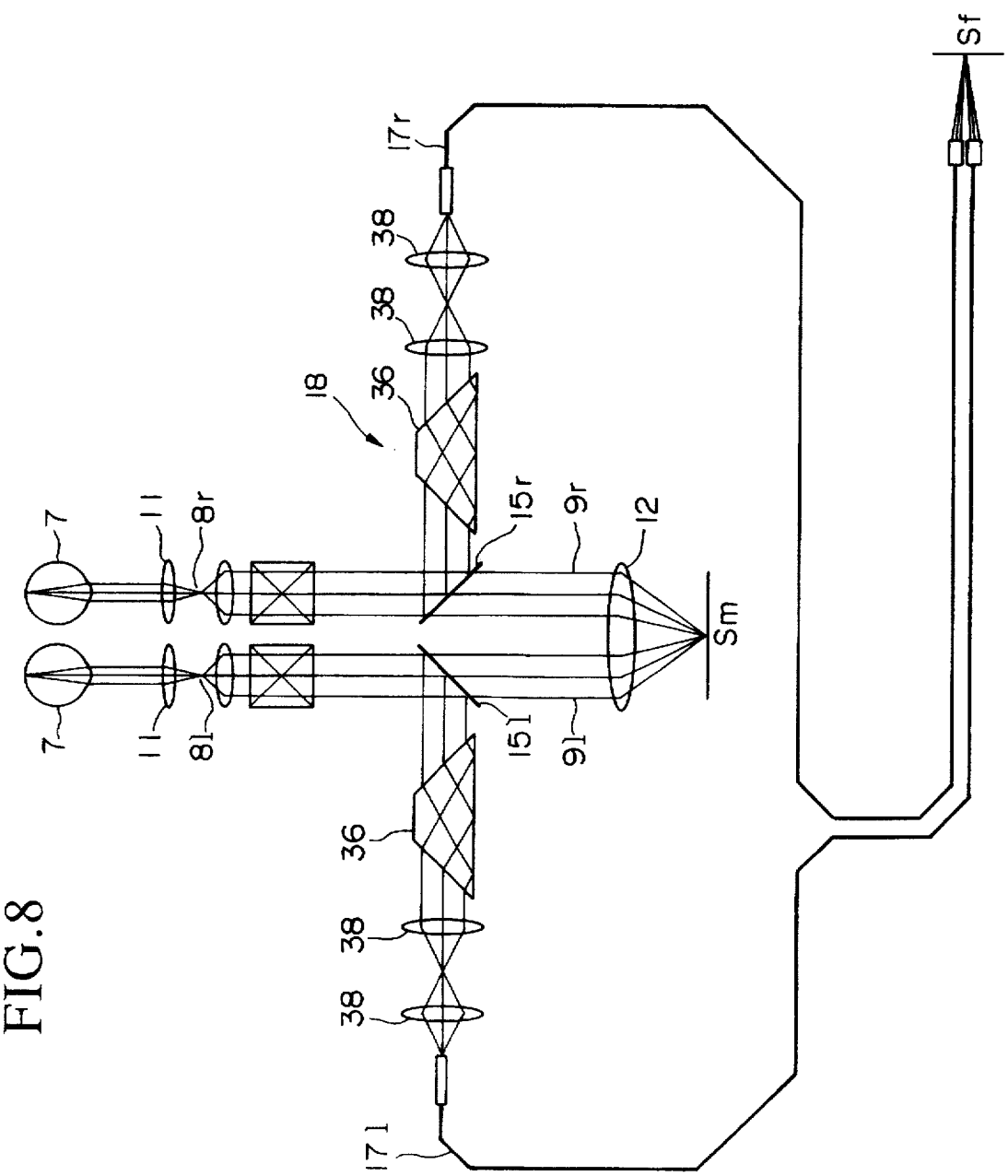

FIG. 8 is a diagram of the optical path provided for explaining the image aligner.

Figure 9:
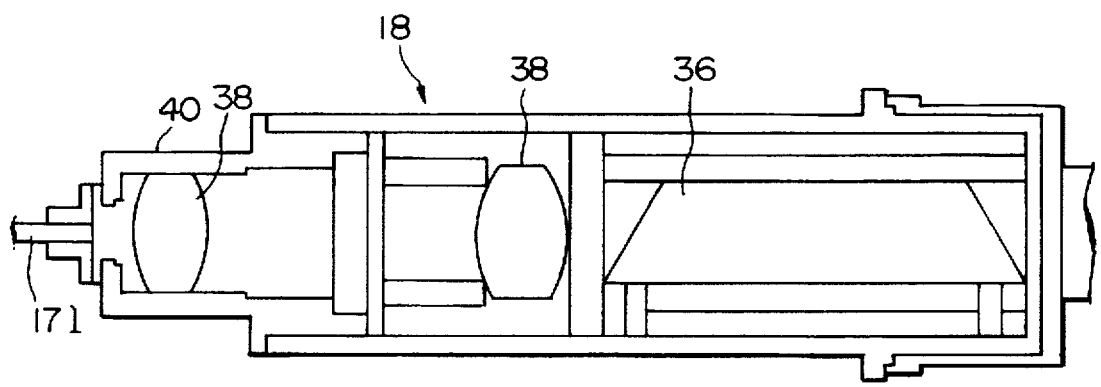

FIG. 9 is view in lateral cross-section showing the left half of the image aligner.

Figure 10:
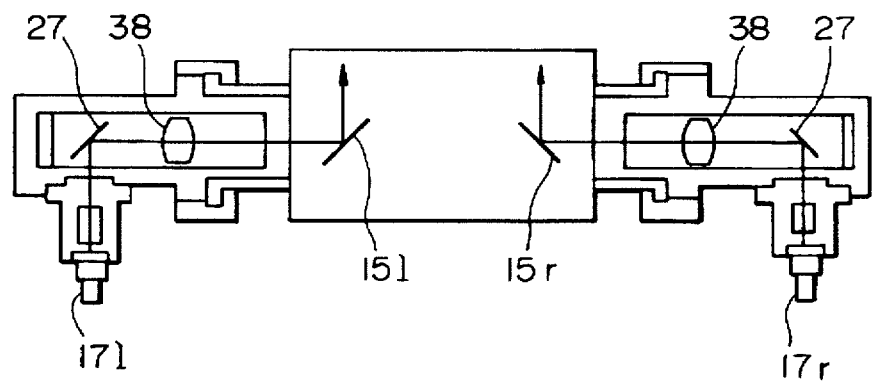

FIG. 10 is a view in lateral cross-section showing another example of the image aligner.

Figure 11:
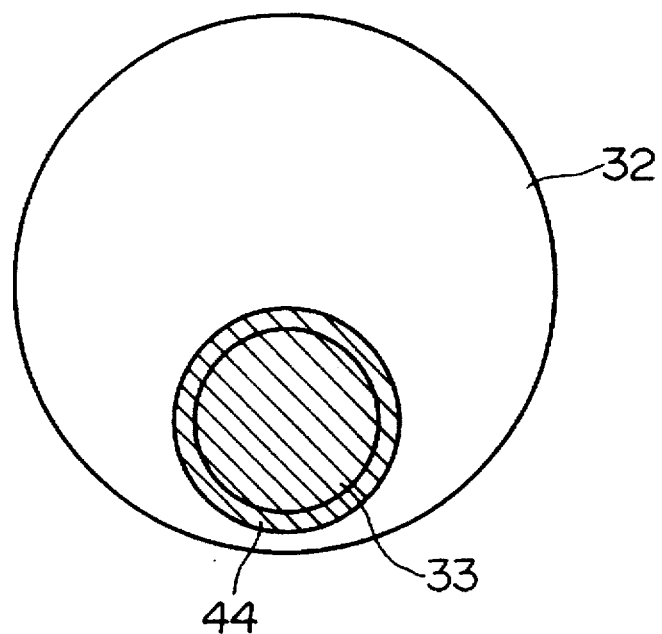

FIG. 11 is a plan view showing an example of an image.

Figure 12:
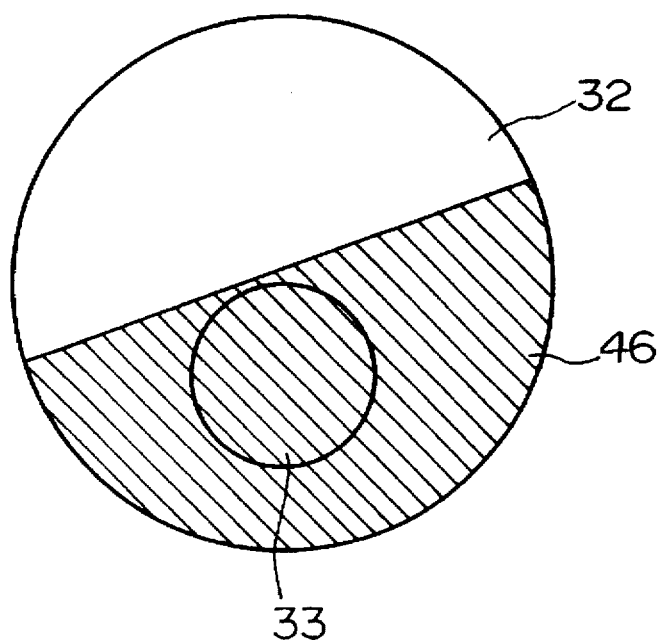

FIG. 12 is a plan view showing an example of an image.

Figure 13:
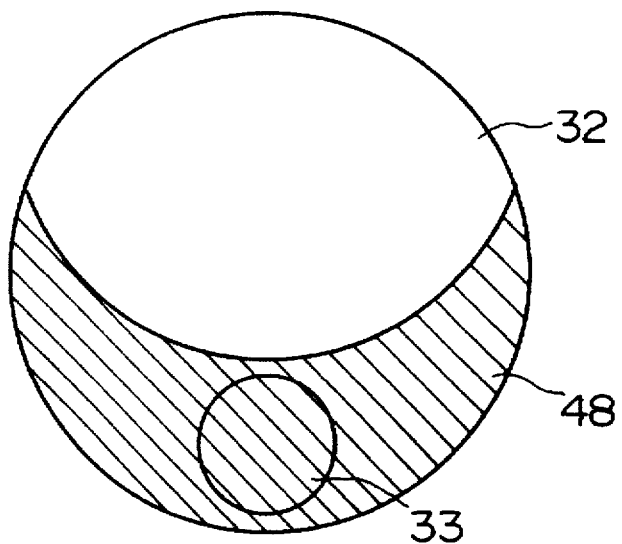

FIG. 13 is a plan view showing an example of an image.

Figure 14:
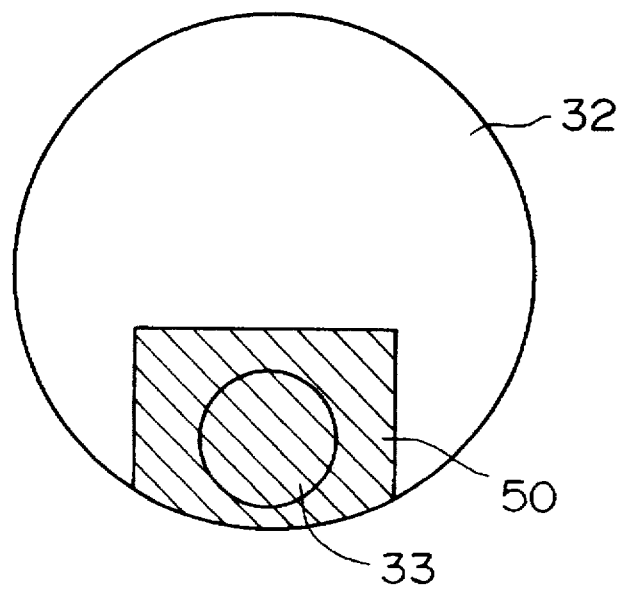

FIG. 14 is a plan view showing an example of an image.

Figure 15:
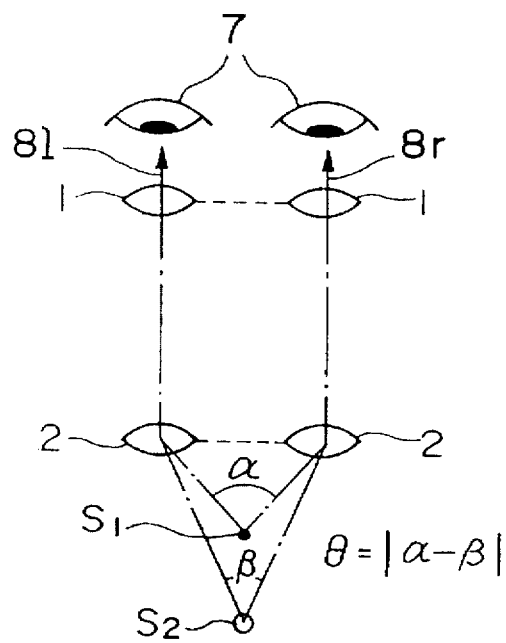

FIG. 15 is a diagram of an optical path in a conventional stereomicroscope.

Figure 16:
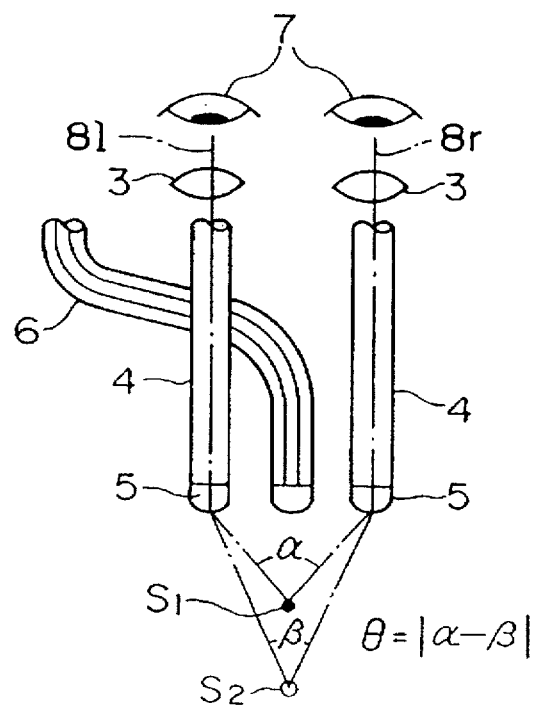

FIG. 16 is a diagram of an optical path in a conventional endoscope.

BEST MODE FOR CARRYING OUT THE INVENTION

Embodiment 1

Figure 1:
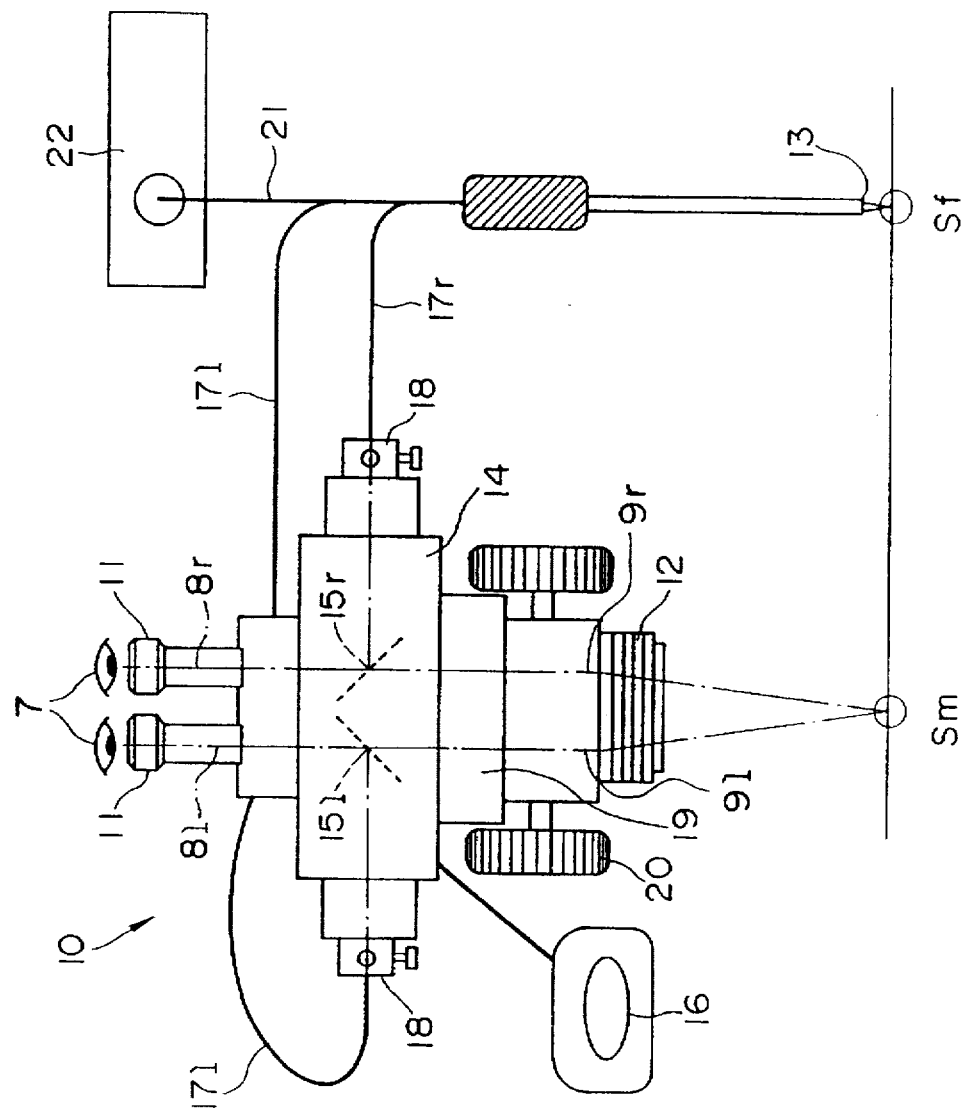
FIG. 1 is a front view showing one embodiment of the present invention.

FIG. 1 shows one embodiment of the device for stereoscopic visualization of the present invention. This device 10 is provided with eyepieces 11, which has a pair of optical paths 8l,8r corresponding respectively to the left and right eyes of an observer 7, a stereomicroscope objective 12, a stereoscopic fiberscope objective 13, and an optical path switcher 14. The respective pairs of optical paths of stereomicroscope objective 12 and stereoscopic fiberscope objective 13 can be freely changed by means of optical path switcher 14, with one pair of the optical paths joining with the pair of optical paths of eyepieces 11.

Optical path switcher 14 internally houses a pair of reflecting mirrors 15l,15r. These reflecting mirrors 15l,15r, which are coupled and revolve, are driven by a foot switch 16 so that each can simultaneously switch the left eye optical path 8l and the right eye optical path 8r to either the stereomicroscope objective or the stereoscopic fiberscope objective.

Respective image aligners 18 for left eye optical path 8l and right eye optical path 8r are provided between optical path switcher 14 and stereoscopic fiberscope objective 13, adjacent to optical path switcher 14. The image aligners 18 and stereoscopic fiberscope objective 13 are joined by flexible image fibers 17l,17r corresponding respectively to the left eye optical path and the right eye optical path. Image aligners 18 are designed so that the position, orientation, and focus of each of the left and right images can be adjusted by moving or rotating the optical axes of the image fibers connected thereto.

Stereoscopic fiberscope objective 13 has image fibers 17l,17r connected to the objective lens at its tip, and light guides 21 disposed parallel to the image fibers.

Figure 2:
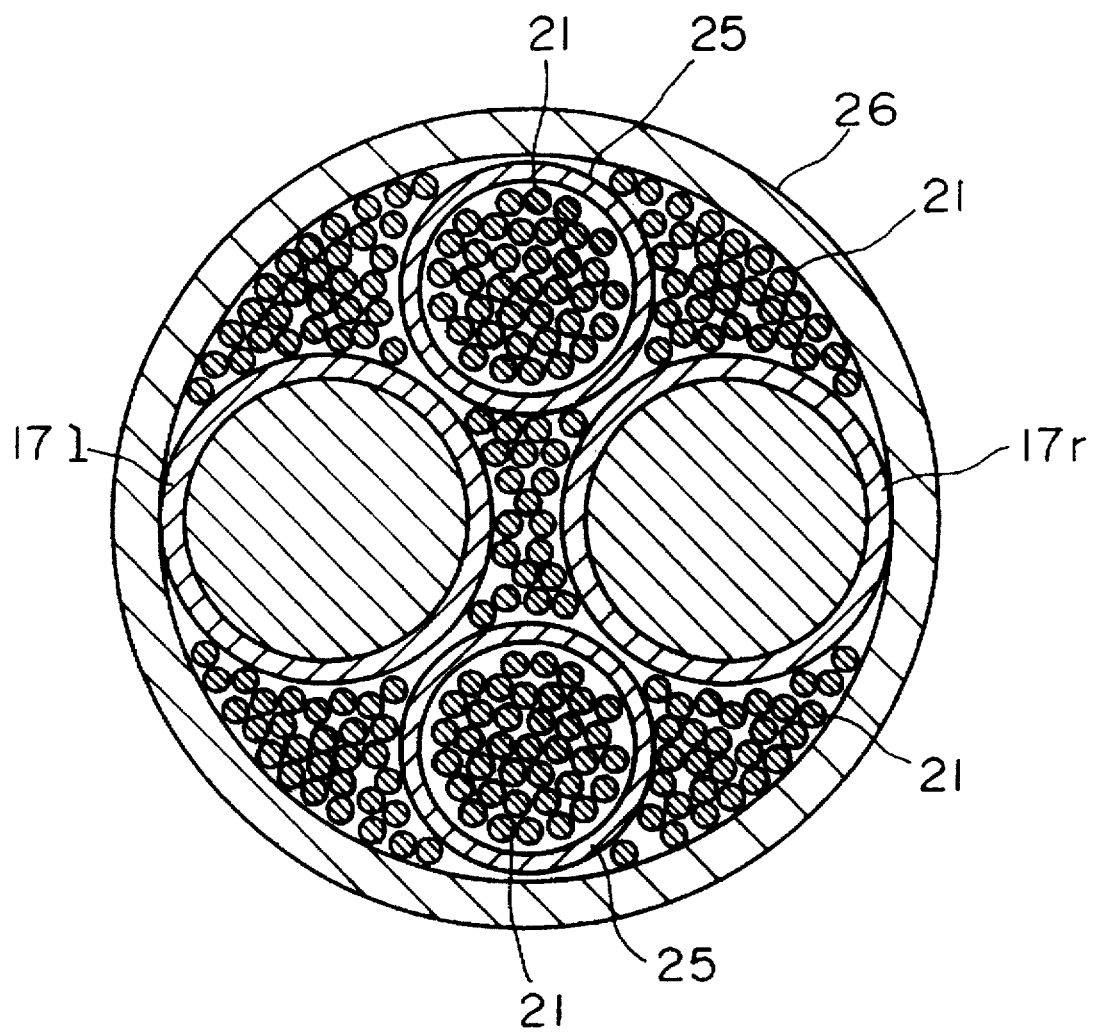
FIG. 2 is a cross-sectional view of a fiberscope.

A cross-section of the fiberscope, in which image fibers 17l,17r and light guides 21 form a bundle, is shown in FIG. 2. Image fiber 17l, used for the left eye optical path, image fiber 17r, used for the right eye optical path, and a plurality of light guides 21,21 . . . are wrapped together inside fiberscope 26. Cylindrical spacers 25,25 are disposed in fiberscope 26 shown in FIG. 2, for separating image fiber 17l and image fiber 17r. Light guides are also disposed inside these spacers 25.

4

Light guides 21 are connected to fiberscope light source 22. Illuminating light from fiberscope light source 22 which has passed through light guide 21 illuminates an object Sf observed with the stereoscopic fiberscope.

It is desirable to provide an illuminating lens to the tip of light guides 21 in the same way that an objective lens is provided to the tip of image fibers 17l,17r.

Each image fiber 17l,17r comprises an image circle, wherein approximately 1,500 to 50,000 GeO2-SiO2 cores as a quartz glass fiber are disposed at fixed intervals inside a common clad of SiO2 or SiO2-F, and SiO2 jacket which covers this image circle. Further, the entire image fiber is covered with a resin such as a silicon resin or a UV hardening resin. The diameter of the cores is 2 μm to 10 μm and the diameter of the image fiber is 125 μm to 2000 μm, so that the diameter of the image fiber is 135 μm to 3000 μm when the protective covering layer is included.

Each of these image fibers 17l,17r is housed in a guide tube which guides the image fiber. Stainless steel or a resin such as polyimide, fluorinated ethylene propylene, ETFE, polytetrafluoroethylene, polyethylene, polypropylene, polyvinyl or the like may be employed as the material for the guide tube. The inner diameter of the guide tube is 135 μm to 3,500 μm, while the outer diameter is 150 μm to 4,000 μm.

The light guide is a fiber consisting of a multicomponent glass, quartz glass, plastic or the like, with a diameter of 10 μm to 2,000 μm.

The spacer consists of stainless steel, quartz glass or a resin such as polyimide, fluorinated ethylene propylene, ETFE, polytetrafluoroethylene, polyethylene, polypropylene, polyvinyl or the like, and has a diameter of 100 μm to 2,000 μm. From 0 to 10,000 light guides are inserted in this cylindrical spacer. In addition, this spacer is not absolutely necessary, but may be eliminated by fixing together a specific number of light guides. Further, a pair of image fibers are disposed inside a coated tube, to be explained below, so as to mutually contact with one another. Provided their deflection can be controlled, the spacers may be omitted.

These image fibers, light guides and the like are disposed inside and covered by a tube consisting of stainless steel or a resin like polyimide or polytetrafluoroethylene. The thickness of this coated tube is 0.3 to 10 mm.

The length of the fiberscope is 0.2 to 10 m in total, with the length of the inserted portion being 10 to 350 mm.

The thus-described fiberscope is formed in the following way.

First, rod lenses which bring together image formation characteristics (angle of view, focus position, contrast, size, etc.) are attached to the tips of the image fibers which bring together transmission characteristics (contrast, length of radius, etc.). From among those produced, a pair of image fibers with attached rod lens which bring together the transmission and image formation characteristics are selected. Then, a pair of rounded light guide fibers, wherein the light guides either fill a cylindrical spacer or the light guides are fixed together at the tips with an adhesive or the like, is formed, with the tips being adhered together.

Next, the pair of guide tubes which guide the image fibers are disposed inside the coated tube. Further, a pair of spacers is also disposed inside the coated tube, with light guides inserted to fill the spaces thereof. Then, the entire structure is sealed.

The tip is then polished, and the image fiber with its attached lens is inserted into the guide tube, and sealed.

The following is a concrete example of a fiberscope which satisfies these conditions.

The entire length of the fiberscope employed here is 2.0 m, with the length of the inserted portion being 30 mm. The coated tube employed here is of stainless steel and has an outer diameter of 1.0 mm, with an inner diameter of 0.9 mm.

A polyimide tube with an outer diameter of 0.4 mm and an inner diameter of 0.36 mm is employed for each image fiber 17l,17r. Further, these image fibers have 5,000 pixels with a pixel diameter of 300 μm; SiO2-GeO2 is employed for the cores which compose the pixels, with the clad consisting of SiO2-F. The image fibers are provided with a protective resin layer consisting of a UV hardening resin of thickness 25 μm.

A polyimide tube of outer diameter 0.3 mm and inner diameter 0.25 mm is employed for the cylindrical spacers.

A multicomponent glass fiber of diameter 30 μm is employed for the lightguides. Out of 194 lightguides, 37 lightguides are used to fill the inside of each spacer, with the remaining 120 lightguides used to fill the outside space.

For example, an object can be observed in the following way employing a device for stereoscopic visualization of the above construction. First, the optical path switcher 14 is set to stereomicroscope objective 12, and the left eye optical path 8l at eyepiece 11 and the left eye optical path 9l of the stereomicroscope objective 12 are joined, while the right eye optical path 8r of eyepiece 11 and the right eye optical path 9r of the stereomicroscope objective 12 are joined. Accordingly, observer 7 recognizes an image of observed object Sm from the stereomicroscope.

Further, as observed object Sm is observed through eyepieces 11, the focus of stereomicroscope main body 19, which includes eyepieces 11 and stereomicroscope objective 12, is adjusted by turning focus adjustment knob 20.

Next, optical path switcher 14 is switched to stereoscopic fiberscope objective 13. In other words, by changing the angle of reflecting mirrors 15l,15r of optical path switcher 14, the left eye optical path 8l at eyepiece 11 and the image fiber 17l are joined, while the right eye optical path 8r at eyepiece 11 and the image fiber 17r are joined. At the same time, left eye optical path 9l and right eye optical path 9r from the stereomicroscope objective are blocked by reflecting mirrors 15l,15r.

Fiberscope light source 22 is turned on, and the observed object Sf is illuminated via lightguides 21.

Thus, the observer recognizes the observed object Sf from the stereoscopic fiberscope.

Further, when optical path switcher 14 is switched from the stereomicroscope to the stereoscopic fiberscope objective 13, the focus and relative disposition of the image observed will be disrupted. In order to avoid this, one or both of the left and right image aligners 18 can be adjusted in advance, thus eliminating the need for adjustment later.

Further, it makes no difference whether the observed object Sf is in the field of view of the stereomicroscope main body 19 or not. In other words, if observed object Sf is included in the observed object Sm, then observation with the stereoscopic fiberscope can be carried out by enlarging a portion of the observed object Sm. Further, if observed object Sf is not included in observed object Sm, then the area which is not observed with the stereomicroscope can be observed with the stereoscopic fiberscope.

In the above-described device for stereoscopic visualization, the observer 7, with his eyes placed against the eyepieces 11, operates the foot switch 16 with his foot to switch between the image from the stereomicroscope and the image from the stereoscopic fiberscope. Accordingly, the hands are not hampered in the switching operation, and the eyes do not have to be removed from the eyepieces 11. Thus, observation of either object Sm or object Sf can be carried out promptly at any time.

In particular, the image from the stereomicroscope and the image from the stereoscopic fiberscope can be viewed without requiring a high degree of electrical conversion employing an LCD or the like.

Figure 3:
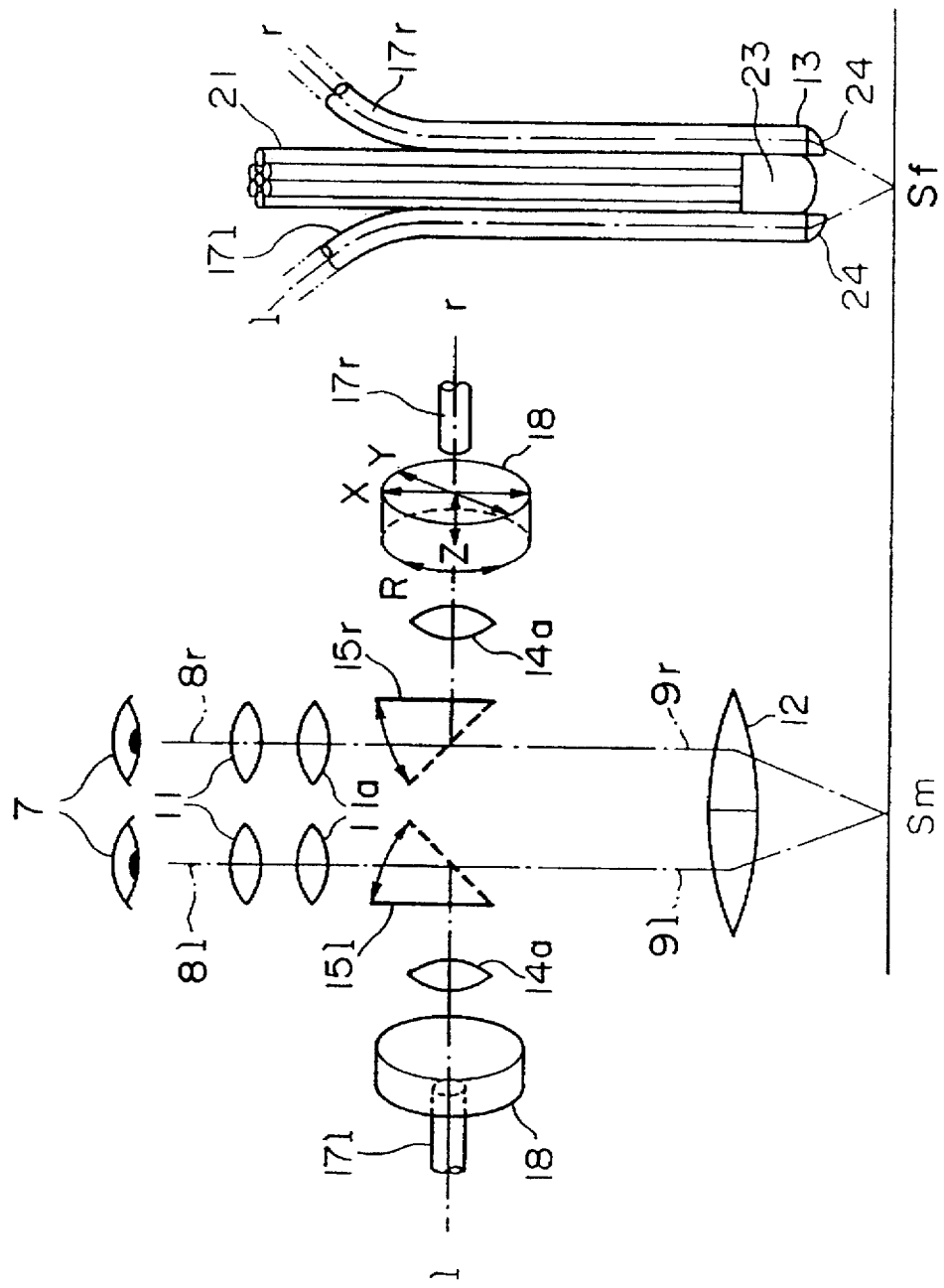
FIG. 3 is a diagram of the optical path in one embodiment of the present invention.

The preceding embodiment will now be explained further employing the optical path system diagram shown in FIG. 3.

Bidirectional reflected light from observed object Sm is separated and received at objective lens 12. Light from the image respectively passes through left eye optical path 9l and right eye optical path 9r at the objectives, and then passes through an erected relay optical system 11a which has a plurality of lens, etc. Then the light from the image passes through the left eye optical path 8l and the right eye optical path 8r of eyepieces 11. In this state, the reflective lens 15l,15r of the optical path switcher are both parallel to the optical path. The light from the image from objective lenses 12 is not blocked by optical path switcher 14, but proceeds directly to eyepieces 11. Observer 7 thus observes object Sm as a stereoscopic image.

When optical path switcher 14 is switched, reflecting mirrors 15l,15r block the optical paths 9l,9r from the stereomicroscope objective. At the same time, they reflect light from the image incidenting from the stereoscopic fiberscope objective 13 via image fibers 17l,17r, and transmit the light to eyepieces 11 via erected relay optical system 11a.

Observed object Sf is illuminated with light irradiated from illuminating lens 23 via light guides 21 which are disposed inside the stereoscopic fiberscope parallel to each image fiber 17l,17r and preferably comprise a plurality of optical fibers. Further, this reflected light is received as light from left and right images by objective lenses 24 which are attached respectively to the ends of each image fiber 17l,17r. The reflected light is then transmitted to the image aligners 18 by image fibers 17l,17r for the left eye optical path 8l and right eye optical path 8r respectively. It is preferable that these image fibers 17l,17r be formed as respective fiber bundles for transmitting images, and be image fibers which are multicore type optical fibers so that a very small diameter can be obtained.

The light from the left and right images transmitted via image fibers 17l,17r respectively can undergo left and right asymmtrical refraction or rotation. Thus, if this light is received at eyepieces 11 which are combined with stereomicroscope objective 12, the image is not adjusted with respect to a position or orientation that will definitely enable observation of a stereoscopic image. Accordingly, the incorrect position or orientation of the light from the left and right images is adjusted using image aligners 18, the reflecting mirrors and the like, prior to being transmitted to optical path switcher 14. Image aligners 18 are provided to the respective output terminals of image fibers 17l,17r, and can move the output terminals in the direction of the optical path (z) and in the two directions (x,y) perpendicular to (z). Further, image aligners 18 are designed so that they can be fixed in position by providing a rotation R. Further, adjustment in the x and y directions can also be carried out by means of the reflecting mirrors. Thus, by these means, adjustment can be performed to enable observation of the light from image from the stereoscopic fiberscope objective 13 as a stereoscopic image. Provided that there is no change in the scope, the adjustment of image aligners 18 does not need to be carried out during observation.

The light of the image which is erected on the left and right by image aligners 18 is reflected respectively at reflecting mirrors 15 via image fiber relay lens 14a, reaches eyepiece 11 via erected relay optical system 11a, and is observed by the observer 7 as a stereoscopic image.

Optical path switcher 14 employs reflecting mirrors in the above embodiment, but is not restricted thereto. For example, half-mirrors or prisms may also be used. Further, the switching of the optical paths can be carried out by rotating the reflecting mirrors, half-mirrors, prisms or the like around an axis perpendicular to the optical paths as described above. However, in addition, a solenoid or the like may also be employed as a driving means to move the reflecting mirrors or the like into and out of transsection with the optical paths.

Further, in the case where a half-mirror or small mirror is employed, switching may be accomplished without requiring a drive system by employing a method wherein either the light incidenting on the stereomicroscope objective or the light incidenting on the stereoscopic fiberscope objective is blocked.

While only a single observer was present in the preceding embodiment, the present invention's device for stereoscopic visualization is not limited thereto. For example, each optical path 8l,8r between eyepieces 11 and erected relay optical system 11a can be separated into 2 optical paths. One of the separated optical paths is joined to eyepieces 11, and the other separated optical path is joined to another set of eyepieces. By this means, a plurality of observers can view an image with the device for stereoscopic visualization. Further, the other separated optical path can be connected to a TV camera, with the left and right images being alternately shown on a monitor. Then, by applying a lens with an electric shutter which opens and closes alternately on the left and right in synchronization with this, the image on the monitor can be observed. In this case, then, not only the surgeons, but any number of people can simultaneously observe the stereoscopic image.

The aligners 18 will now be explained in greater detail.

As shown in FIG. 8, when left eye optical path 8l and right eye optical path 8r which pass through eyepieces 11 are joined with left eye optical path 9l and right eye optical path 9r from objective lens 12 of the stereomicroscope by means of the driving of reflecting mirrors 15l,15r, then left eye optical path 8l and right eye optical path 8r come in contact with left eye optical path image fiber 17l and the right eye optical path image fiber 17r of the stereoscopic fiberscope.

While there is no problem in the connection of optical paths 8l,8r which pass through eyepieces 11 with each of the optical paths 9l,9r from the objective lens 12 of the stereomicroscope, distortion in the position or orientation of the image may arise when optical paths 8l,8r which pass through eyepieces 11 are connected to the optical paths of the stereoscopic fiberscope. Thus, adjustment is carried out using image aligners 18 or reflecting mirrors 15l,15r. In image aligners 18, focus and optical axis adjustments are carried by each of the lens 38,38 . . . . while at prism 36, left-right reversal of the image is performed.

A compositional member such as shown in FIG. 9 is used for image aligner 18. In the case of this device, light from the image which has entered image aligners 18 from image fiber 17l is adjusted to the optimal position and orientation by extending or rotating optical axis adjustment cell 40, which is equipped with a lens 38, and by the left-right reversal of the light at a prism 36 through which it is passed. This light from the image is then transmitted to the eyepieces.

Further, as shown in FIG. 10, by employing an image fiber connection method, the optical axis from the image fiber can also be adjusted. In other words, the light from image fiber 17l is incidented from below, and passes through the lens. Then, it undergoes left-right reversal at reflecting mirrors 27.

By forming this type of image aligner, which is connected to a fiberscope and is attached to a stereomicroscope, as a single unit, attachment of a variety of commonly used stereomicroscopes is possible, widening the application thereof.

Embodiment 2

Figure 4:
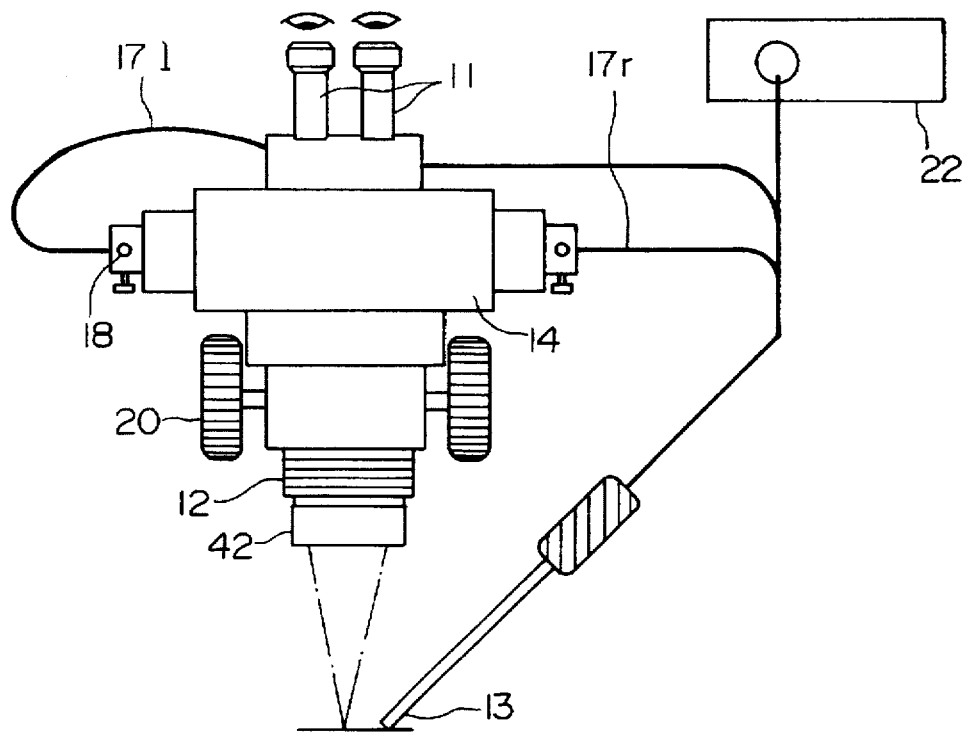
FIG. 4 is a front view showing another embodiment of the present invention.
Figure 5:
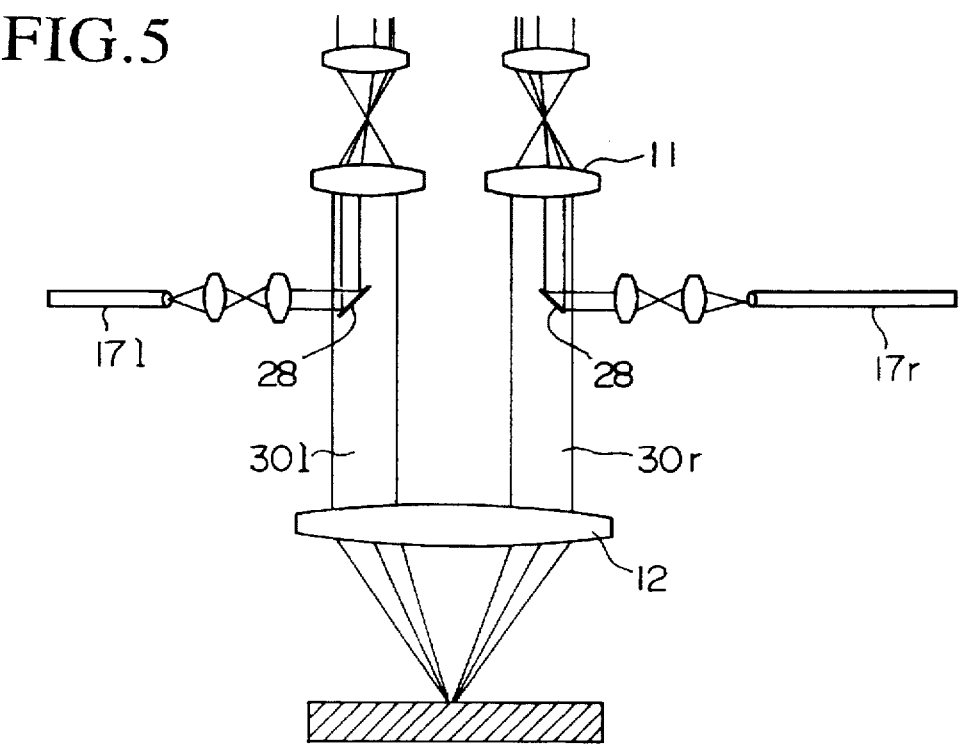
FIG. 5 is a diagram of the optical path of the embodiment of the present invention shown in FIG. 4.

Further, a device for stereoscopic visualization can be composed as shown in FIGS. 4 and 5. In this device, reflecting mirrors 28,28 which are provided along the optical path from the stereoscopic fiberscope are provided along optical paths 30l,30r which join eyepieces 11 and the objective 12 of the stereomicroscope. In this case, the device is designed so optical paths 30l,30r are not completely blocked by reflecting mirrors 28.

This device is formed so that images 33l,33r from the fiberscope are placed into the images 32l,32r of the stereomicroscope in the left and right eyepieces 11, as shown in FIG. 6. Accordingly, when the same object is observed with the stereomicroscope and the fiberscope, the observer sees a portion of he image 32 from the stereomicroscope in the image 33 from the fiberscope, as is shown in FIG. 7.

Additionally, it is noted here that half-mirrors may also be employed in place of the reflecting mirrors.

Further, the position of image 33 from the fiberscope in image 32 from the stereomicroscope can be adjusted by means of the image aligner or the inclination of reflecting mirror 28.

In order to observe the image from the stereoscopic fiberscope, illumination from a light guide provided to the stereoscopic fiberscope is necessary. Accordingly, by stopping the illumination from the light guide, image 33 from the fiberscope disappears, and the observer sees only image 32 from the stereomicroscope. In other words, by manipulating the light guide, the image from the fiberscope can be "turned on and off". Further, by placing or removing a blocking cap on the tip of the stereoscopic fiberscope objective, the image from the stereoscopic fiberscope can be "turned on and off".

When a reflecting mirror 28 is provided to the portion of the stereomicroscope inside the optical path 30, the field of vision of the entire object does not change, but the quantity of light decreases. Accordingly, it is desirable to provide an object light source 42 for illuminating the observed object at objective 12 of the stereomicroscope. In this case, it is desirable to lower the degree of illumination so that light does not strike the position of image 33 from the stereoscopic fiberscope or its surrounding area. Image 33 from the stereoscopic fiberscope is generally darker compared with image 32 from the stereomicroscope. Thus, in order to make the image 33 from the stereomicroscope clearer, the area around the image should be darkened.

For example, as shown in FIG. 11, only the position of image 33 from the stereoscopic fiberscope and its periphery 44 are darkened in image 32 from the stereomicroscope. Further, as shown in FIGS. 12, 13, and 14, it is desirable to darken areas 46, 48, 50 which form the image 33 of the stereoscopic fiberscope.

As a method to darken the area around the position of the image from the stereoscopic fiberscope, it is preferable to provide to object light source 42 a mask for blocking the light from object light source 42 from illuminating that position.

Further, when the amount of light of the image from the stereoscopic fiberscope is considerably less compared to the amount of light from the image from the stereomicroscope and the image from the stereoscopic fiberscope cannot be observed because the image therefrom is not formed in the dark area, the object light source 42 of the stereomicroscope, and not the fiberscope light source 22, is manipulated. Then, on/off control of the formation of the image 33 from the stereoscopic fiberscope inside image 32 from the stereomicroscope can also be carried out by means of whether or not the periphery of the image formed from the stereoscopic fiberscope is darkened. For example, on/off control of the formation of the image from stereoscopic fiberscope 33 inside image 32 from the stereomicroscope can be carried by attaching or removing the mask.

Further, the amount of light of the image from the stereomicroscope is influenced by the area of the reflecting mirror 28 of the optical path 30. Thus, the control of the increase or decrease in the amount of light can be carried out by moving reflecting mirror 28 from the optical path 30.

In the device for stereoscopic visualization having the structure shown in FIGS. 4 and 5, the observer can view the image 32 from the stereomicroscope and the image 33 from the stereoscopic fiberscope simultaneously. Accordingly, if the observer is viewing the image from the stereomicroscope, and then wishes to view the image from the stereoscopic fiberscope, he need not remove his eyes from the stereomicroscope to do so.

In particular, this device for stereoscopic visualization enables the formation of image from a stereoscopic fiberscope inside the image from a stereomicroscope by means of an optical method alone, and not by the employment of an electronic circuit. Thus, the device is simple, accurate and can be achieved at low cost.

Industrial Applicability

The device for stereoscopic visualization according to the present invention enables an observer to quickly switch, between or simultaneously view, an image from a stereomicroscope objective and an image from a stereoscopic fiberscope objective, without removing his eyes from the eyepieces. Accordingly, a surgical procedure can be carried out on an affected area while observing images of the area obtained from a stereomicroscope and a stereoscopic fiberscope.

We claim:

1. A device for stereoscopic visualization comprising:

an eyepiece having optical paths respectively corresponding to a left eye and a right eye of an observer;

a stereomicroscope including a stereomicroscope objective along the optical paths of the eyepiece;

a stereoscopic fiberscope including a stereoscopic fiberscope objective; and reflecting mirrors disposed on the optical paths of the eyepiece and connecting the eyepiece to the stereoscopic fiberscope objective and wherein the reflecting mirrors are disposed in a portion of the optical paths connecting the eyepiece to the stereomicroscope objective to reflect image beams from the stereoscopic fiberscope parallel to and inside image beams from the stereomicroscope objective to thereby form an image from the stereoscopic fiberscope in a portion of an image from the stereomicroscope.

2. The device according to claim 1, wherein the image from the stereoscopic fiberscope is formed in a darkened portion of the image from the stereomicroscope.

3. A device for stereoscopic visualization comprising:

an eyepiece having an optical path;

a stereomicroscope including a stereomicroscope objective along the optical path of the eyepiece;

a fiberscope including a fiberscope objective; and a reflecting mirror disposed on the optical path of the eyepiece and connecting the eyepiece to the fiberscope objective and wherein the reflecting mirror is disposed in a portion of the optical path connecting the eyepiece to the stereomicroscope objective to reflect image beams from the fiberscope parallel to and inside image beams from the stereomicroscope objective to thereby form an image from the fiberscope in a portion of an image from the stereomicroscope.

* * * * *